United States Patent [19]

Malhotra et al.

[11] Patent Number: 4,499,277

[45] Date of Patent: Feb. 12, 1985

[54] REDUCTION OF TRICHLOROMETHYLPYRIDINES TO DICHLOROMETHYLPYRIDINES

[75] Inventors: Sudarhshan K. Malhotra, Walnut Creek; Jon A. Orvik, Danville, both of Calif.

[73] Assignee: The Dow Chemical Company, Midland, Mich.

[21] Appl. No.: 475,020

[22] Filed: Mar. 14, 1983

Related U.S. Application Data

[63] Continuation-in-part of Ser. No. 256,863, Apr. 24, 1981, abandoned.

[51] Int. Cl.$^3$ .............................................. C07D 213/26
[52] U.S. Cl. ....................................... 546/346; 546/345
[58] Field of Search ........................................ 546/346

[56] References Cited

U.S. PATENT DOCUMENTS 3,420,833   1/1969   Taplin ................................. 546/180
3,591,596   7/1971   Wang et al. ......................... 546/294
4,062,962   12/1977  Noveroske .......................... 424/263
4,143,144   3/1979   Tobol et al. ......................... 424/263
4,260,766   4/1981   Morris ................................. 546/303

OTHER PUBLICATIONS

Hawley, The Condensed Chemical Dictionary, Tenth Edition, p. 1048, 1981.

Primary Examiner—Alan L. Rothman
Attorney, Agent, or Firm—S. Preston Jones; Ronald G. Brookens

[57] ABSTRACT

2(6)-(Trichloromethyl)pyridines are reduced to the corresponding 2(6)-(dichloromethyl)pyridines by treatment with a strong base and an anionic reductant derived from a reductant source material selected from the group consisting of dialkylphosphite and trialkylphosphite said treatment taking place in the presence of a polar, non-hydroxylic solvent and/or a phase transfer catalyst.

8 Claims, No Drawings

REDUCTION OF TRICHLOROMETHYLPYRIDINES TO DICHLOROMETHYLPYRIDINES

RELATIONSHIP TO PRIOR APPLICATION

This is a continuation-in-part of Application Ser. No. 256,863, filed Apr. 24, 1981.

BACKGROUND OF THE INVENTION (Dichloromethyl) substituted pyridines are known compounds which find utility as pesticides for the control of plant, insect and fungal pests, among others, and as intermediates for preparing compounds having the above utilities. Representative patents which teach such uses include U.S. Pat. Nos. 3,420,833; 3,591,596; 4,062,962 and 4,143,144.

Various derivatives of phenoxypyridine, such as the compounds made from cyano(6-phenoxy(or substituted phenoxy))-2-pyridine methanol, are useful as pesticides. One method of preparing this class of compounds is through an intermediate derivative of alpha-(dichloromethyl)pyridine which is conveniently prepared by reducing the corresponding trichloromethyl derivative.

(Dichloromethyl) substituted pyridines have been prepared from (trichloromethyl) substituted pyridines by a variety of procedures. A few of these procedures include, for example, dehydrochlorination over a palladium catalyst in the presence of formic acid, electrolytic reduction and reductions employing either zinc or stannous chloride with hydrochloric acid and the like. Another method is taught in U.S. Pat. No. 4,260,766 wherein the reduction is conducted with metallic iron or a ferrous iron compound. The prior processes, while producing the desired product, have not found wide success because of one or more shortcomings such as expense of reagents, slow reaction rate, poor selectivity to the desired product or the difficulty in treating waste streams for recycle and/or disposal. The present invention is a process for carrying out the reduction with greater flexibility and specificity than that found using conventional reducing agents.

SUMMARY OF THE INVENTION

The invention herein described is a process for reducing a trichloromethyl substituent in the 2-position of a pyridine ring to a dichloromethyl group which comprises treating said 2-(trichloromethyl)pyridine with a strong base to maintain the reaction under slightly basic conditions and a reductant source material selected from the group consisting of dialkylphosphites and trialkyl phosphites; said treatment being carried out in the presence of either a polar, non-hydroxylic solvent and/or a phase transfer catalyst at a temperature of from about $-20°$ C. to about $160°$ C. for a time sufficient to convert at least some of the trichloromethyl groups to dichloromethyl groups.

As used herein, the term alkyl refers to an alkyl having from one to about four carbon atoms, such as, for example, methyl, ethyl, n-propyl, i-propyl, n-butyl, sec-butyl and t-butyl. The term aryl refers to an aromatic hydrocarbyl group such as, for example, phenyl or tolyl.

In general, (trichloromethyl)pyridine derivatives suitable for use in the process may be represented as follows:

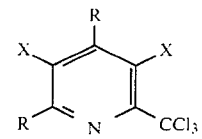

wherein X independently and in each occurrence represents chlorine or hydrogen and R, independently and in each occurrence, represents hydrogen, $C_1$–$C_4$ alkoxy, chlorine, phenoxy, or substituted phenoxy. As used herein, the term substituted phenoxy refers to a phenoxy moiety containing one or more substituents which do not detrimentally affect the reduction of the trichloromethyl group. Such a substituted phenoxy moiety may contain one or more substituents such as, for example, alkyl, alkoxy, or halo.

Representative (trichloromethyl)pyridines which can be employed in the practice of the present invention include, among others
2-chloro-6-(trichloromethyl)pyridine,
2-chloro-4-methoxy-6-(trichloromethyl)pyridine,
3,5-dichloro-2-(trichloromethyl)pyridine,
4,6-dichloro-2-(trichloromethyl)pyridine,
3,4,5,6-tetrachloro-2-(trichloromethyl)pyridine,
6-phenoxy-2-(trichloromethyl)pyridine,
6-phenoxy-5-fluoro-2-(trichloromethyl)pyridine,
6-(4-chlorophenoxy)-2-(trichloromethyl)pyridine
6-(3-chlorophenoxy)-2-(trichloromethyl)pyridine
6-(4-fluorophenoxy)-2-(trichloromethyl)pyridine,
and 6-(4-methoxyphenoxy)-2-(trichloromethyl)pyridine.

As used herein, the term polar, non-hydroxylic solvent refers to those solvents which provide sufficient solubility for the reactants to function as a medium for the reaction. A number of readily available polar, non-hydroxylic solvents have been found suitable for use in this process, such as, for example, N-methylpyrrolidone, dimethylformamide, dimethysulfoxide, hexamethylphosphoric triamide and diglyme.

Normally, instead of using a polar, non-hydroxylic solvent, a quaternary ammonium phase transfer catalyst may be used. A number of quaternary ammonium phase transfer catalysts suitable for use in the process are commercially available. Those skilled in the art are familiar with such catalysts—for example, tetra-n-butylammonium chloride methyl tri-n-butylammonium chloride and benzyl triethylammonium chloride.

In carrying out the process of the present invention, the reduction is carried out at a temperature of from about $-20°$ C. to about $160°$ C., with a temperature range of from about $0°$ C. to about $40°$ C. being preferred. At temperatures below about $-20°$ C. the reduction proceeds so slowly that it would not be commercially feasible to carry it out. At higher temperatures appreciable degradation of the reactants and desired products tends to occur. Generally, when the more reactive reductants and/or more reactive (trichloromethyl)pyridine compounds are employed, the reaction can be simply carried out at ambient temperatures. The pressure at which the reaction occurs is not critical, and usually the process is performed at atmospheric pressure.

The strong base is either an inorganic base such as an alkali metal hydroxide (sodium, potassium, lithium or cesium hydroxide) or an organic base such as, for example, choline, a compound of the formula $(CH_3)_3N^{\oplus}-CH_2-CH_2OH/OH^{\ominus}$ or alkali metal alkoxides such as sodium methoxide. Of the above bases, sodium hydroxide and potassium hydroxide are preferred.

A solvent is not always necessary for the reaction to proceed and if the pyridine reactant or the reducing agent can also act as the solvent, the reaction may be carried out in the absence of additional solvent, ordinarily by the inclusion of a phase transfer catalyst in the reaction mixture.

It is preferred that the various reactants be present in about equimolar amounts.

The following examples will serve to further illustrate the invention, but should not be interpreted as a limitation thereon.

EXAMPLE 1

In a reaction vessel fitted with a magnetic stirrer, 2.31 grams (10 mmole) of 2-chloro-6-(trichloromethyl)pyridine was dissolved in 25 ml of N-methylpyrrolidone. To this mixture was added 2.0 grams of 50% aqueous sodium hydroxide and 1.29 grams (10.2 mmole) of dimethyl phosphite. Within five minutes the temperature rose from 24° C. to 55° C. Analysis by glc indicated a ratio of 97.6/1.7 for reduced product to starting material. The reaction mixture was poured into 100 ml of water and the oil which separated was crystallized to form 1.4 grams of 2-chloro-6-(dichloromethyl)pyridine (mp 50°–53° C.). The yield was calculated to be 71% of theoretical.

EXAMPLE 2

(a) Reduction of 6-phenoxy-2-(trichloromethyl)pyridine with 2 molecular proportions of trimethyl phosphite and 3.4 moles of KOH per mole of 6-phenoxy-2-(trichloromethyl)pyridine, resulted in a 75% conversion of the trichloromethyl group in diglyme after 2 hours at 100° C. Good selectivity for the desired dichloromethyl compound was evident from glc examination of an aliquot of the reaction mixture.

(b) Under otherwise essentially the same conditions as in (a), 6-chloro-2-(trichloromethyl)pyridine was 80% converted, with good selectivity for the dichloromethyl derivative, after being treated with the same reductant overnight at room temperature.

EXAMPLE 3

In a stirred reaction vessel was placed 2.31 grams (0.010 mole) of 2-chloro-6-(trichloromethyl)pyridine, 20 ml of N-methylpyrrolidone and 1.35 grams (0.011 mole) of dimethylphosphite. The mixture was heated for about 2½ hours. During this period, 50 percent aqueous sodium hydroxide was slowly added to maintain the pH slightly basic. At the end of the reaction period, there was 1% of the pyridine starting material remaining. Additionally, it was found that 0.0225 mole of the aqueous sodium hydroxide had been added. The reaction mixture was poured into water, extracted with methylene chloride, dried and the methylene chloride removed by evaporation, to yield 1.6 grams (80% of theoretical) of crude 2-chloro-6-(dichloromethyl)pyridine.

EXAMPLE 4

2-Phenoxy-6-(trichloromethyl)pyridine (2.89 grams (0.010 mole) was dissolved in 25 ml of N-methylpyrrolidone. To this mixture was added, at room temperature, 1.17 grams (0.0106 mole) of dimethylphosphite followed by 1.0 grams (0.125 mole) of 50% aqueous sodium hydroxide. A slight exotherm from 25° C. to 56° C. occurred within five minutes and analysis by glc indicated an 89/11 ratio of the dichloromethyl to trichloromethyl product. A further addition of 0.23 gram of dimethylphosphite and 0.5 gram of 50% aqueous sodium hydroxide converted 100% of the trichloromethyl reactant to the corresponding dichloromethyl product.

EXAMPLE 5

2-Phenoxy-6-(trichloromethyl)pyridine (2.89 grams (0.010 mole) was dissolved in 25 ml of N-methylpyrrolidone. To this mixture was added 1.5 grams of 50% aqueous sodium hydroxide and then 1.17 grams (0.0106 mole) of dimethylphosphite. This was followed by another 0.5 gram of 50% aqueous sodium hydroxide since the pH of the reaction mixture was about neutral. The dichloromethyl/trichloromethyl ratio at this point was 95/5. Another 0.12 gram of dimethylphosphite was added and the ratio became 100/0.

What is claimed is:

1. A process for reducing the trichloromethyl group in a (trichloromethyl)pyridine compound to a dichloromethyl group which comprises treating said compound with a strong base and a reductant source material selected from the group consisting of dialkylphosphites and trialkyl phosphites wherein each alkyl group is of from one to four carbon atoms, said treatment being carried out in the presence of a polar, non-hydroxylic solvent providing sufficient solubility for the reactants and/or a quaternary ammonium phase transfer catalyst at a temperature of from about $-20°$ C. to about 160° C. for a time sufficient to convert to the corresponding (dichloromethyl)pyridine compound.

2. The process of claim 1 wherein the reaction is carried out at a temperature of from about 0° to about 40° C.

3. The process of claim 1 wherein the strong base is sodium hydroxide.

4. The process of claim 2 wherein the trichloromethyl substituent is reduced using dimethyl phosphite as the reductant source material and N-methylpyrrolidone as the reaction medium.

5. The process of claim 1 wherein said (trichloromethyl)pyridine compound is 6-chloro-2-(trichloromethyl)pyridine.

6. The process of claim 1 wherein said (trichloromethyl)pyridine compound is 6-phenoxy-2-(trichloromethyl)pyridine.

7. The process of claim 5 wherein the reduction is carried out using N-methylpyrrolidone as the reaction medium and dimethyl phosphite as the reductant source material.

8. The process of claim 7 in which sodium hydroxide is employed as the strong base.

* * * * *